United States Patent [19]

Gee et al.

[11] Patent Number: 5,200,557

[45] Date of Patent: Apr. 6, 1993

[54] PROCESS FOR PREPARATION OF CRUDE TEREPHTHALIC ACID SUITABLE FOR REDUCTION TO PREPARE PURIFIED TEREPHTHALIC ACID

[75] Inventors: John C. Gee, Aurora; Jeffrey I. Rosenfeld, Schaumburg; Thomas M. Bartos, Wheaton, all of Ill.

[73] Assignee: Amoco Corporation, Chicago, Ill.

[21] Appl. No.: 821,490

[22] Filed: Jan. 15, 1992

Related U.S. Application Data

[63] Continuation-in-part of Ser. No. 685,221, Apr. 12, 1991, abandoned.

[51] Int. Cl.$^5$ ............................................. C07C 51/43
[52] U.S. Cl. .................................... 562/486; 562/414; 562/487; 562/608
[58] Field of Search ................ 562/414, 486, 487, 608

[56] References Cited

U.S. PATENT DOCUMENTS

| | | | |
|---|---|---|---|
| 3,584,039 | 6/1971 | Meyer | 562/487 X |
| 4,314,073 | 2/1982 | Crooks | 562/416 |
| 4,438,279 | 3/1984 | Packer et al. | 562/416 |
| 4,485,244 | 11/1984 | Fox et al. | 562/487 X |

*Primary Examiner*—José G. Dees
*Assistant Examiner*—Vera C. Clarke
*Attorney, Agent, or Firm*—Gunar J. Blumberg; Wallace L. Oliver; Frank J. Sroka

[57] ABSTRACT

A process is disclosed for counter-current positive displacement of an aliphatic carboxylic acid of 1 to 5 carbon atoms from a filter cake of an aromatic polycarboxylic acid containing the aliphatic carboxylic acid wherein mother liquor retained by the aromatic polycarboxylic acid has a concentration of the aliphatic carboxylic acid of 5000 ppmw, or less, based upon weight of the aromatic polycarboxylic acid present. This method is useful for the manufacture of crude terephthalic acid which is used after purification for the preparation of polyesters used for the manufacture of fabrics, fibers and plastic bottles.

8 Claims, No Drawings

PROCESS FOR PREPARATION OF CRUDE TEREPHTHALIC ACID SUITABLE FOR REDUCTION TO PREPARE PURIFIED TEREPHTHALIC ACID

This is a continuation-in-part of application Ser. No. 685,221 filed Apr. 12, 1991, now abandoned.

FIELD OF THE INVENTION

The field of this invention relates to the preparation of crude terephthalic acid by filtration and counter-current washing by water to prepare an aqueous slurry suitable for further processing to prepare purified terephthalic acid wherein the concentration of acetic acid retained in the washed filter cake is equal to or less than 5000 parts per million by weight (ppmw). An aqueous slurry thereby prepared is suitable for a reduction process. In one aspect, this invention relates to the preparation of an aqueous slurry of crude terephthalic acid suitable for a reduction process in the presence of a Group VIII metal catalyst. In another aspect, this invention relates to the preparation of an aqueous slurry of crude terephthalic acid suitable for hydrogenation of the crude terephthalic acid wherein the crude terephthalic acid has been prepared by oxidation of paraxylene in a solvent comprising acetic acid and the acetic acid is replaced by water in a positive displacement method in a procedure of counter-current flooded water washing under pressure. This process eliminates the need for a drying process previously used to remove the acetic acid by evaporation from the crude terephthalic acid. This process of counter-current flooded water washing under pressure of the crude terephthalic acid also operates to reduce the amount of wash water, to decrease the content of residual impurities in crude terephthalic acid, to recycle and recover the acetic acid, and/or decrease the load on downstream waste treatment equipment. In another aspect of this invention, the field of this invention relates to a process for positive displacement of aliphatic carboxylic acids from slurries of crude polycarboxylic acids prepared by oxidation of alkyl aromatics such as paraxylene, metaxylene, diisopropylbenzene, diethylbenzene and 2,6-dimethyl naphthalene in the presence of an aliphatic carboxylic acid of 1 to 5 carbon atoms wherein the aliphatic carboxylic acid of 1 to 5 carbon atoms is replaced by water in a counter-current method to permit reduction of the impurities in the aqueous slurry of crude polycarboxylic acid, in the presence of a Group VIII metal catalyst and hydrogen, and the aliphatic carboxylic acid of 1 to 5 carbon atoms can be recovered for recycle upstream. The field of this invention further relates to a process for preparing crude terephthalic acid suitable for reduction to prepare purified terephthalic acid, by hydrogenation in an aqueous medium in the presence of a Group VIII catalyst and hydrogen.

BACKGROUND OF THE INVENTION

Usually terephthalic acid is produced by a liquid phase oxidation of p-xylene and/or p-toluic acid in a solvent comprising an aliphatic carboxylic acid such as acetic acid. Terephthalic acid is of great commercial importance and is widely used for the production of various different polymers, such as fiber-forming polyesters. A process for preparing polyesters of terephthalic acid, particularly polyethylene terephthalate, comprises a direct condensation of terephthalic acid with the respective polyalcohol. For example, terephthalic acid is reacted with ethylene glycol to form bis($\beta$-hydroxyethyl) terephthalate which is then polymerized in a second stage. This direct condensation process is simpler than other known methods such as transesterification of dimethyl terephthalate with the appropriate glycol. However, the direct esterification can desirably require the use of highly purified terephthalic acid. In order to be suitable for the production of polyester fibers, terephthalic acid must be substantially free of any contaminants which lower the melting point of the polyester and/or cause coloration of the polyester. In fact, some impurities which are contained in crude terephthalic acid are color-forming precursors. Additionally, some impurities act as chain terminators in the process to prepare polyesters.

All these impurities have not yet been identified. However 4-carboxybenzaldehyde which is an intermediate oxidation product and which in the following is abbreviated as 4-CBA, generally is found in crude terephthalic acid. It is known that the degree to which coloration is induced is less if the 4-CBA content of the terephthalic acid is low. While pure 4-CBA itself can promote coloring during polymerization, this impurity is a convenient tracer for evaluating the degree to which terephthalic acid has been refined. A process which can reduce the 4-CBA content of terephthalic acid reduces also the content of color-forming precursors.

From U.S. Pat. No. 3,584,039 issued to Delbert H. Meyer, incorporated by reference, it is known that fiber-grade terephthalic acid may be prepared by purifying crude terephthalic acid by means of a reduction procedure. The process is essentially comprised of treating an aqueous solution of crude terephthalic acid with hydrogen in the presence of a supported or unsupported Group VIII metal catalyst, whereby the metal and the support are insoluble in the solution under the working conditions. By this process, the amounts of 4-CBA and other coloring impurities contained in terephthalic acid are reduced by formation of removable products. Purified terephthalic acid is then recovered by crystallization, filtration to recover the crystalline product and drying.

As noted above, the oxidation of p-xylene is in the presence of an aliphatic carboxylic acid such as acetic acid as solvent. However, the aliphatic carboxylic acid must be removed before hydrogenation of the crude terephthalic acid. The aliphatic carboxylic acid can act as a poison for the hydrogenation catalyst.

Methods have been proposed for replacement or extraction of the acetic acid from the oxidation effluent with water. For example, U.S. Pat. No. 3,839,436 teaches contacting an oxidation slurry with water, wherein water is introduced into the bottom of a displacement zone, to contact the oxidation effluent in a vertical chamber to effect precipitation of the product acid through the column of water and to remove an aqueous slurry suitable for catalytic purification from the bottom of the column. In another example, European Patent Application, Publication No. EPO 321 272 A1, teaches a process for exchanging or dispersing a medium of a terephthalic acid slurry by introducing an aliphatic carboxylic acid slurry of terephthalic acid into a multi-stage column at the upper part thereof and introducing water at the lower part thereof to form an upflowing stream of water in the multi-stage column, while a sedimentation of terephthalic acid particles is effected inside the multi-stage column, and withdrawing an aqueous aliphatic carboxylic acid solution from the upper part of the multi-stage column, and an aqueous slurry of terephthalic acid from the lower part of the multi-stage column. In the one example, the aqueous slurry of terephthalic acid contained 30,000 ppmw of acetic acid.

These methods suffer from the problem that they do not comprise a positive method of displacing acetic acid from the acetic acid slurry of crude terephthalic acid but rely upon precipitation or sedimentation of the crude terephthalic acid through a column of water.

In another method, International Patent Application No. PCT/JP 89/00529, International Publication WO 89/11323 teaches washing terephthalic acid crystals in a rotary vacuum filter wherein a slurry of terephthalic acid is filtered with suction, the slurry and filtrate being maintained under pressure to keep the temperature and pressure at levels which prevent the filtrate liquor from being supersaturated and thus clogging the filter member. Suction filtration is performed and the terephthalic acid crystals are lifted out of the slurry, as filter cake as the filter member rotates, the slurry being located at the bottom of the filter, the filtrate also being located at the bottom of the filter. The filter cake is thereupon washed in a washing area at the top of the rotating filter drum, the washing solution falling downward into a storage area. The wash solution is sprayed onto the filter cake, falling downward into the storage area, and draining with suction. Positive pressures applied to the slurry and filtrate are at relatively low levels, ranging from 0.5 kg/cm2abs to 5.5. kg/cm2abs. Temperature is in the range of from 90° to 150° C.

This method of washing filter cake suffers from the problems that suction, or vacuum, filtration tends to limit the pressure which can be applied to the process to atmospheric pressure. Spray washing tends to cause channeling of the filter cake with lessened penetration of the filter cake by the washing solution.

It is therefore an object of this invention to provide a method for displacing acetic acid from a slurry of crude terephthalic acid in an acetic acid medium wherein the acetic acid is displaced from the slurry of crude terephthalic acid by a positive displacement method using pressure filtration of the crude terephthalic acid slurry in a method of counter-current flooded water washing, also termed plug flow washing, of the filter cake, followed by reslurrying of the crude terephthalic acid in an aqueous medium suitable for a reduction process in the presence of a Group VIII metal catalyst. The concentration of acetic acid retained in the filter cake is equal to or less than 5000 ppmw.

It is an object of this invention to provide a method for displacing acetic acid from a slurry of crude terephthalic acid in an acetic acid medium wherein the acetic acid is displaced from the slurry of crude terephthalic acid by a positive displacement method using filtration of the crude terephthalic slurry wherein the concentration of acetic acid retained in the filter cake is equal to or less than 5000 ppmw without the need of a drying process to remove the acetic acid in the filter cake by evaporation through application of heat.

It is further an object of this invention to provide an improved process for preparation of crude terephthalic acid by oxidation of an alkyl aromatic in an acetic acid medium wherein the crude terephthalic acid prepared thereby has a concentration of retained acetic acid equal to or less than 5000 ppmw in the absence of application of heat to drive off retained acetic acid from the crude terephthalic acid product.

SUMMARY OF THE INVENTION

A process is disclosed for preparation of crude terephthalic acid having a retained acetic acid concentration equal to or less than 5000 ppmw wherein the crude terephthalic acid is suitable for a reduction process to prepare purified terephthalic acid. The crude terephthalic acid is prepared by oxidation of an alkyl aromatic in an acetic acid medium. The reduction of the crude terephthalic acid to prepare purified terephthalic acid is in an aqueous medium in the presence of a Group VIII metal catalyst and hydrogen. The crude terephthalic acid in the acetic acid medium is pressure filtered in a positive displacement counter-current method, using water to displace the acetic acid in a procedure of flooded water washing under a pressure gradient of from about 0.5 psi to about 65 psi over the system pressure to form a washed filter cake having a retained acetic acid concentration equal to or less than 5000 ppmw. The washed filter cake is thereupon slurried in water for the reduction procedure.

DETAILS OF THE INVENTION

In an embodiment of this invention, an alkyl aromatic, such as paraxylene and/or paratoluic acid, is oxidized in an acetic acid medium with molecular oxygen in the presence of a catalyst system containing bromine and one or more heavy metals such as cobalt, manganese and the like. Although this method is well-known in the art and is commercially used, the oxidation reaction results in impurities which must be removed or rendered colorless to obtain a fiber-grade terephthalic acid. The principal use of captive and non-captive terephthalic acid is and has been for the manufacture of high molecular weight polyesters for fiber and film manufacture.

From U.S. Pat. No. 3,584,039, it is known that fiber grade terephthalic acid can be prepared by purifying crude terephthalic acid by means of a reduction procedure. The process is essentially comprised of treating an aqueous solution of crude terephthalic acid with hydrogen in the presence of a supported or unsupported Group VIII metal catalyst wherein the metal and the support are insoluble in the solution under the working conditions. By this process, intermediate oxidation products, such as 4-carboxybenzaldehyde (4-CBA) and other coloring impurities in terephthalic acid are reduced and form removable or colorless products. Purified terephthalic acid is then recovered by crystallization and dried.

Although the above procedure has various advantages, problems remain in that the acetic acid in the oxidation procedure needs to be substantially removed from the terephthalic acid before hydrogenation. Acetic acid can act as a poison for the hydrogenation catalyst, thus reducing catalyst life. The separation of the acetic acid from the terephthalic acid by centrifugation, or filtration and drying can involve loss of the acetic acid unless acetic acid recovery systems are utilized.

In the separation and hydrogenation of crude terephthalic acid from acetic acid, see EPO 321 272 A1, one method that has been employed is to exchange a dispersing medium containing the crude crystals of terephthalic acid from an oxidation reaction medium of acetic acid, by using a multi-stage column to disperse the crude crystals in water to obtain an aqueous slurry of terephthalic acid containing 0.03 parts by weight of acetic acid, 30,000 ppmw. The aqueous slurry can be hydrogenated by contact with hydrogen gas to improve the solubility of the impurities and to remove the impurities by dissolution into the solvent. In the process of this method, residual slurry acetic acid is greater than 5000 ppmw.

Despite the above solution to the problem of separating crude terephthalic acid from acetic acid, an efficient separation of crude terephthalic acid crystals from acetic acid and the preparation of the crude crystals in a form suitable for hydrogenation can require a filtration or centrifugation procedure, a drying device and a storage procedure. Equipment costs can be significant and each step can involve attendant equipment problems. There are thus strong incentives to simplify the procedure and reduce equipment costs.

In the process of the instant invention, the crude terephthalic acid crystals in the acetic acid medium from a crystallizer are filtered to develop a filter cake about 0.5 inch in depth, preferably to about 2 to 8 inches, the mother liquor being recirculated to the oxidation reactor. Upon obtaining a preferred minimum height of filter cake, about 2 inches to about 8 inches, the stream of acetic acid slurry containing the crude terephthalic acid crystals is interrupted and replaced by a counter-current water stream at a pressure gradient over the system pressure, sufficient to cause a reservoir buildup of water over the level of the filter cake sufficient in depth to cover the surface of the filter cake, preferably to a depth of about 0.25 inch. The applied positive pressure over the system pressure can be at a minimum positive pressure sufficient to displace the acetic acid from the filter cake by water of at least about 0.5 psi. Preferably a pressure over the system pressure of from about 5 psi to about 65 psi is applied to the water stream to displace the acetic acid from the filter cake in a positive displacement method. System pressure can be atmospheric pressure or at a positive or negative differential from atmospheric pressure. The water-washed cake of crude terephthalic acid is thereupon discharged from the filter to a slurry tank wherein additional water is added to form a slurry. System temperature is typically at an elevated temperature within the range of from about 65.5° C. (150° F.) to about 191° C. (375° F.). The crude terephthalic acid is thereupon hydrogenated in the presence of a Group VIII metal catalyst and hydrogen to prepare purified terephthalic acid.

It has been found that counter-current positive displacement of acetic acid in the filter cake using water as the displacing medium in a filtration cycle permits an efficient exchange of the acetic acid solvent from the oxidation reaction for a medium comprising water as a major component with recovery of the crude acid from the slurry of acetic acid and terephthalic acid. The positive displacement of the acetic acid in the filter cake removes the acetic acid from the terephthalic acid and replaces the acetic acid by water.

The amount of an aqueous acetic acid solvent which can be retained in the filter cake of crude terephthalic acid before counter-current washing can be in the range of from about 8 wt % to about 20 wt % of the total weight of the filter cake, typically about 9 wt % to about 12 wt %, of which 90 wt % is acetic acid and the remaining 10 wt % is water.

Because of the size of the crude terephthalic acid crystals and the tendency of the terephthalic acid in the filter cake to retain acetic acid, typical filtration techniques are unsuitable to remove completely residual acetic acid from the filter cake, requiring the inclusion of a drying step. Although the size problem can be overcome by use of suitably sized filter cloth, filtration and water washing is typically unsuccessful in removing acetic acid wherein a vacuum is used or wherein pressure filtration is used without use of a method of plug flow washing or flooded water washing. Such vacuum or pressure filtration procedures result in the channeling of the cake and the water wash does not penetrate the cake.

In the process of the instant invention it has been found that unexpected efficiencies of removal of acetic acid can be obtained by counter-current pressure displacement washing of the filter cake comprising crude terephthalic acid. Acetic acid in crude terephthalic acid can be reduced to 5000 ppmw, or less. Utilization of added stages of pressure counter-current displacement washing decreases the amount of water required as a result of the counter-current washing procedure.

Counter-current washing is defined as washing a series of filter cells containing filter cake wherein each filter cell is washed successively in reverse order to degree of contamination.

For example, the addition of water to the process by the method of counter-current positive displacement can reduce the level of acetic acid retained in the cake to 1000 ppm acetic acid. The amount of water required to obtain a retained level of 1000 ppm of acetic acid is lessened by the use of added stages of positive displacement and counter-current washing, the added water being recycled to reduce the total amount added. Thus, in the occasion of use of only one stage of positive displacement washing, it has been found that 0.567 lbs of water recycled to the oxidation process per lb of crude terephthalic acid are required to reduce the level of acetic acid in the cake to 1000 ppm. With counter-current recycle of the wash water, the amount of water required to reduce the level of acetic acid (HAC) in the dry cake to 1000 ppm acetic acid is significantly reduced, as follows:

| Total $H_2O$ Recycled lbs $H_2O$/lb TA | No. Stages | HAc in Dry Cake ppm |
| --- | --- | --- |
| 0.567 | 1 | 1000 |
| 0.231 | 2 | 1000 |
| 0.133 | 3 | 1000 |
| 0.090 | 4 | 1000 |
| 0.066 | 5 | 1000 |

As indicated, the concentration of acetic acid in the filter cake can be reduced with a minimum amount of water added to the process by use of additional stages of positive water displacement. For example, the addition of 0.133 lbs $H_2O$ per lb of crude terephthalic acid with three stages of counter-current positive displacement washing can reduce the concentration of acetic acid to 1000 ppm. With two added stages of counter-current positive displacement washing or a total of five stages, the concentration of acetic can be reduced to 59 ppm. Similarly, if 0.133 lbs of water per lb of crube terephthalic acid are added to the process a reduction of stages of from three stages of counter-current positive displacement washing to one stage causes the concentration of acetic acid to remain at a level of 22,587 ppm, but if 0.133 lbs of water per lb of crude terephthalic acid are added to the process using more stages of counter-current positive displacement washing, the concentration of acetic acid in the cake is as follows:

| | |
|---|---|
| 22,587 ppm HAc | after 1 stage |
| 4,541 ppm HAc | after 2 stages |
| 1,000 ppm HAc | after 3 stages |
| 242 ppm HAc | after 4 stages |
| 59 ppm HAc | after 5 stages |

It is essential therefore that a suitable number of stages of counter-current positive displacement washing be used to minimize total water used in displacement washing. Accordingly, for the process of the instant invention for positive displacement of acetic acid from mother liquor retained in filter cake of crude terephthalic acid to obtain a level equal to or less than about 5000 ppm in the cake by filtration, a multi-stage counter-current filtration of the crude terephthalic acid is used.

An acetic acid slurry containing crystals of crude terephthalic acid is introduced into one or more of a series of filter cells physically situated to permit a filter cake of requisite thickness to develop by passage of a stream of the slurry of crude terephthalic acid. The flow of the slurry of crude terephthalic acid is thereupon interrupted and replaced by a water stream to permit a reservoir buildup to a requisite level. Pressure is applied thereupon to the water stream to displace the acetic acid in the mother liquor retained in the filter cake by positive pressure. Upon displacement of the water reservoir through the filter cake, the filter cake is discharged from the filter by suitable means and the cycle is repeated. The washed filter cake, upon discharge from the filter, can be re-slurried in water to form an aqueous solution suitable for purification by hydrogenation.

A cake depth of terephthalic acid of about 0.5 inch to about 8 inches is suitable. The preferred range is from about 2 to about 8 inches. A filter cake of sufficient thickness to furnish a wash vehicle, i.e., the filter cake, from which a solution containing a solute can be removed efficiently by displacement washing is required. If cake depth is less than about 0.5 inch, retention of acetic acid by the filter cake can occur despite application of wash water because of channeling of wash water through the filter cake. Because of the loss of efficiency in displacement washing of the filter cake by water to remove a solution containing a dissolved solute, a minimum filter cake depth of about 0.5 inch of purified terephthalic acid is useful. As indicated in Example 18, washing efficiency is improved by increased cake thickness.

A minimum liquid height above the cake surface is preferred to ensure that displacement washing occurs. This height must be sufficient to ensure that the cake surface is completely covered with liquid. If the cake surface is not covered with water, bypassing of the wash liquor can occur without complete displacement of mother liquor from the interior of the cake. Because of irregularities in the cake surface, a minimum liquid depth over the cake of about $\frac{1}{4}$" is preferred.

Equipment for performing the requisite cycle can comprise a series of filter cells maintained in a suitable position to permit a water flood to develop over the filter cells. Suitable equipment can comprise a rotary drum filter with multiple filter cells, and fitted with means for discharging washed filter cake from the filter cells. Control means are required for introducing a stream comprising crude terephthalic acid in an acetic acid medium, interrupting the stream to permit introduction of a water stream to cause development of a water reservoir over the filter cake, applying pressure to the water stream to cause positive displacement of the acetic acid in the mother liquor retained in the crude terephthalic acid, repeating the development of a water reservoir over the filter cake for as many counter-current passes as required to develop a minimum concentration of acetic acid in the filter cake and discharging the washed filter cake from the rotary drum filter.

A suitable rotary drum filter which can be adapted to the requirements of the instant invented process is a BHS-FEST (TM) pressure filter, BHS-WERK, Sonthofen, D-8972, Sonthofen, West Germany, although other filters which can accomplish the required cycle of operation can be used. A belt filter such as is available from Pannevis, bv, Utrecht, Holland can be used.

In the operation of the BHS-FEST (TM) filter, a rotary drum contains a series of filter cells located on the periphery of the rotating drum. As the drum rotates, the filter cells receive an acetic acid slurry of crude terephthalic acid and a filter cake builds to a requisite depth. Upon rotation of the drum, the cycle continues by interruption of the feed stream which is replaced by a water stream under pressure to build a reservoir of water over the filter cake to a required depth. Upon further rotation of the drum, the pressure applied to the water reservoir forces the water through the filter cake to displace the acetic acid retained in the crude terephthalic acid. Upon further rotation of the drum, the washing is repeated at least one time, using wash water from a previously washed filter cake in a counter-current procedure, after which the filter cake is discharged from the drum by application of an inert gas under pressure.

The discharged cake containing up to or less than about 5000 ppmw of acetic acid in the crude terephthalic acid is reslurried in water to form a solution wherein the crude terephthalic acid is hydrogenated in the presence of hydrogen and a Group VIII metal catalyst, as taught in U.S. Pat. No. 3,584,039, incorporated herein by reference to exemplify the preparation of purified terephthalic acid from crude terephthalic acid containing 5000 ppmw, or less, of acetic acid.

Although the above description of the process of the instant invention has been directed to the multistage counter-current positive displacement of acetic acid from mother liquor in the preparation of an aqueous solution of crude terephthalic acid, the instant invented process can be applied to the displacement of any 1 to 5 carbon aliphatic monocarboxylic acid from a slurry of crude polycarboxylic acid wherein the said crude polycarboxylic acid has been prepared by oxidation of an alkyl aromatic. Examples of such polycarboxylic acids include trimellitic acid, isophthalic acid, pyromellitic acid, and 2,6-naphthalenedicarboxylic acid.

The following examples illustrate the process of the instant invention but are not intended to limit the scope of the instant invention.

EXAMPLE I

The following example illustrates single stage displacement washing with water to remove acetic acid from a slurry of crude terephthalic acid.

Laboratory filtration experiments were performed in a 350 ml cylindrical glass funnel under vacuum. An 80 micron coarse fritted disc was at the bottom of the funnel. Funnel diameter was 3.25 inches. Crude terephthalic acid used had a mean particle size of 145 microns.

A slurry of crude terephthalic acid and solvent, 90 wt % glacial acetic acid, 10 wt % water, was poured into the funnel. Vacuum, 560 mm Hg, was applied and the liquid was allowed to drain. The slurry was added continuously so that a free liquid level was maintained above the cake forming in the funnel. After the desired cake height had built up, and the free liquid had disappeared from the cake surface, the vacuum was held for an additional 20 seconds and then disengaged. A filter paper was then placed on the cake surface to prevent channeling. The wash liquid was poured into the funnel to create a free liquid layer above the surface. The filter paper was removed and the vacuum again initiated. Wash liquid was added continuously to maintain a free liquid layer above the cake. After the last of the wash liquid disappeared from the cake surface, vacuum was applied for an additional 20 seconds. The vacuum was then removed, the funnel contents weighed and homogenized. Samples were analyzed for solids, wetness (% liquor), and acetic acid concentration on cake.

Slurry concentration was 41 wt. %. Pressure differential between vacuum and ambient pressure was in the range of 10.5 to 10.9 psi. Three stage countercurrent washing was simulated by retaining effluent from each step and using it successively for each wash.

Details are in Table I.

TABLE I

ACETIC ACID DISPLACEMENT BY MULTISTAGE WASHING OF CRUDE TEREPHTHALIC ACID

| Example No. | Slurry | Cake Inches | Feed, wt. % HAc/H$_2$O | Acetic Acid Displaced, %, 3 Washes |
|---|---|---|---|---|
| 2 | HAc/H$_2$O | 2.25 | 90/10 | 94.2 |
| 3 | HAc/H$_2$O | 2.25 | 90/10 | 88.5 |
| 4 | HAc/H$_2$O | 2.25 | 90/10 | 84.8 |
| 5 | HAc/H$_2$O | 2.25 | 90/10 | 87.0 |
| 6 | HAc/H$_2$O | 2.25 | 90/10 | 87.0 |
| 7 | HAc/H$_2$O | 2.25 | 90/10 | 88.1 |
| 8 | HAc/H$_2$O | 2.25 | 86/14 | 97.0 |
| 9 | HAc/H$_2$O | 1.13 | 86/14 | 98.1 |

EXAMPLE 10

The following example illustrates multiple stage displacement washing with water to remove acetic acid from a slurry of crude terephthalic acid.

Pilot plant filtration experiments were performed with a pilot rotary drum pressure filter manufactured by BHS-FEST TM. Total filter area was 0.12 m$^2$. The feed to the filter was created by slurrying crude terephthalic acid with a mixture of acetic acid and water. The crude terephthalic acid (TA) used had a mean particle size of 175 microns.

A slurry was created which consisted of 43 wt % solids. The mother liquor consisted of 90 wt % acetic acid. Initial residual acetic acid on cake was calculated to be 1,193,000 ppmw on dry TA cake. The slurry, approximately 200 gallons, was heated to 190° F. in an agitated kettle. A slip stream from a pump-around loop was diverted to the pilot filter. The pressure of this stream was controlled by a back pressure regulator.

The slurry entered the BHS-FEST TM filter, with the filter cup retaining the cake and the mother liquor passing through the filter cloth for collection. The cake formed had a height of approximately 20 mm. The filter elements containing wet cake were then rotated through, successively, a first dry zone, a first wash zone, a second dry zone, a second wash zone, and a third dry zone. The water reservoir was of a depth of 0.5 inches. Washing was performed by positive displacement pumps using distilled water heated to 190° F. for each wash. Drying was performed by mass flow controllers using dry nitrogen. Wash or dry flow rates for each zone were independently set. After the third dry zone, the cake was discharged by a combination of cake blowback and spring-loaded knife. Residual cake in the cell was then removed by a cloth rinse using distilled water. Each filter cell was then rotated to the feed zone where the entire process would begin again.

Cake analyses of the discharged cake were made by gas chromatographic analysis to determine the residual acetic acid content of the cake as well as the cake wetness (% liquor).

Details are in Table II.

TABLE II

ACETIC ACID DISPLACEMENT BY MULTISTAGE WASHING OF CRUDE TEREPHTHALIC ACID

| Example No. | Speed rpm | cake flow. lb/min | 1st & 2nd wash lb/min water | 1st & 2nd dry SCFH nitrogen |
|---|---|---|---|---|
| 11 | 1.0 | 5.88 | 1.45 | 5.1 |
| 12 | 1.0 | 5.88 | 2.51 | 5.1 |
| 13 | 1.0 | 5.88 | 0.70 | 5.1 |
| 14 | 2.4 | 10.11 | 2.02 | 5.1 |
| 15 | 2.4 | 10.11 | 2.88 | 5.1 |
| 16 | 2.4 | 10.11 | 0.99 | 5.1 |
| 17 | 2.4 | 10.11 | 1.45 | 5.1 |

| Example No. | Feed pressure psig | wash rate lb/lb cake | 3rd dry SCFH N$_2$ | cake wetness wt % liquor |
|---|---|---|---|---|
| 11 | 5 | 0.247 | 21 | 11.6 |
| 12 | 5 | 0.427 | 21 | 12.0 |
| 13 | 5 | 0.119 | 21 | 13.0 |
| 14 | 10 | 0.200 | 21 | 12.9 |
| 15 | 10 | 0.285 | 21 | 13.9 |
| 16 | 10 | 0.098 | 21 | 15.5 |
| 17 | 10 | 0.143 | 21 | 14.4 |

| Example No. | Residual Acetic acid ppmw in wet cake | Mother Liquor Displacement calculated per stage, % |
|---|---|---|
| 11 | 4340 | 80.4 |
| 12 | 2690 | 84.8 |
| 13 | 5570 | 79.0 |
| 14 | 12800 | 68.1 |
| 15 | 9800 | 73.1 |
| 16 | 51600 | 41.6 |
| 17 | 27300 | 55.9 |

EXAMPLE 18

The following example illustrates the effect of cake height on wash efficiency of acetic acid.

Filtration experiments were performed with a leaf filter testing apparatus. The filter consisted of a filter screen held in place with O-rings at the bottom of a stainless steel cylinder. The cylinder was jacketed, which allowed the experiments to be conducted at elevated temperature. The cylinder was also designed so that it could be pressurized.

The experiments were conducted by pouring a 43 wt % terephthalic acid slurry in 90% acetic acid into the apparatus. The slurry was allowed to heat to 190° F. At the start of the experiment, a valve on the bottom of the apparatus was opened and the mother liquor drained, forming a cake. The filter was then depressurized and an amount of wash water added to the filter. A spatula was used to direct the water to the side of the filter apparatus so that the cake surface would not be disturbed. The amount of water used was equal to ⅛ of the weight of the wet cake. The filter was then pressured up to the same pressure at which the cake was formed and the wash liquor drained from the cake. The cake was then blown dry for a period of time equal to the time required to form the cake.

Cake analyses were made to determine the residual amount of acetic acid retained by the cake. It was found that wash efficiency (as measured by retained acetic acid) improved as cake height increased. Details are in Table III.

TABLE III

| Example | Forming Pressure psig | Cake Height mm | Acetic Acid on Cake, ppmw Wet Cake |
|---|---|---|---|
| 19 | 5 | 20 | 12700 |
| 20 | 10 | 22 | 12300 |
| 21 | 20 | 69 | 7250 |
| 22 | 40 | 73 | 7080 |
| 23 | 20 | 99 | 5590 |
| 24 | 40 | 102 | 5960 |
| 25 | 40 | 133 | 5410 |

Note: 25.4 mm = 1 inch

EXAMPLE 26

The following example illustrates multiple stage countercurrent displacement washing with water to remove acetic acid from a slurry of crude terephthalic acid.

Slurry, containing 43 wt % crystallized TA solids and mother liquor, is fed to a BHS-FEST(TM) rotary pressure filter at 6.1 lb/min flow rate, 30 psig pressure, and 198° F. temperature. A BHS-FEST(TM) filter is employed to separate the solids from the mother liquor, wash the solids countercurrently in three stages, dry to remove excess moisture, and discharge the solids at atmospheric pressure. The filter housing is divided into seven chambers to perform five different operations—cake formation, countercurrent displacement wash (3 chambers), cake drying, cake discharge, and filter cloth rinse. The filter drum, operating at a speed of 0.5 rpm, is divided into twenty filter cells. The total filter cloth area available on the drum is about 1.3 ft².

As the filter operates continuously, all of the operations—cake formation, countercurrent displacement wash, cake drying, cake discharge, and filter cloth rinse—occur simultaneously. The operation is described by illustrating the history of one filter cell.

The filter cell rotates into the cake formation chamber. The feed slurry, containing about 43 wt % TA solids, 198° F. temperature, and about 90 wt % acetic acid in the mother liquor is pumped continuously into the chamber at 30 psig pressure. As the filter cell rotates through the chamber, the solids build up on the filter cloth to a 1 inch cake thickness. The mother liquor passes through the filter cloth into an internal pipe in the filter. The pressure of the mother liquor in this internal pipe is about atmospheric pressure. The mother liquor is recycled back to the process by pumping.

The filter cell, now containing a formed cake, leaves the cake formation chamber and rotates into a series of three wash displacement chambers operated countercurrently. The first wash chamber uses wash which is pumped from the discharge of the second wash chamber. The second wash chamber uses wash which is pumped from the third wash chamber. The third wash chamber uses clean water pumped continuously into it. The discharge from the first wash chamber is recycled back to the process by pumping or may be sent to a dehydration tower to separate the water and acetic acid, the acetic acid being subsequently recycled back to the process. The temperature in each wash chamber is about 200° F. The filter drum is steam heated to ensure temperature uniformity of the washes. The pressure of each wash inlet varies between 8 and 15 psi above ambient pressure and is the amount of pressure necessary to enable the flow of discharged wash liquor from the previous stage to be pushed through the following stage. The discharge from each wash stage is effectively at atmospheric pressure. The clean water entering the third stage is thus reused in the two previous stages and, via the effectiveness of displacement washing, effectively removes acetic acid from the filter cake.

The washed cake in the filter cell leaves the displacement wash chambers and enters the cake drying chamber. Compressed inert gas, at a pressure of about 20 psig, is introduced continuously into the drying chamber to remove excess water from the filter cake. This excess water is combined with the discharge from the third wash chamber and is used as the feed wash for the second wash chamber.

The filter cell then rotates from the drying chamber into the cake discharge chamber. The cake is discharged from the filter using a spring loaded knife blade at a flow rate of about 3 lbs/min. The final cake has an acetic acid concentration suitable for further purification. The final level of acetic acid is dependent upon the water addition ratio, or ratio of water recycled back to the oxidation process to the TA cake prepared for further purification. The amount of clean water used in the third wash chamber is directly related to the water addition ratio.

After discharging the cake, the filter cell is rinsed with water in the filter cloth rinse chamber to remove any traces of undischarged cake. The filter cell then enters the cake formation chamber and repeats the process.

Data for relevant experiments are indicated in Table IV.

TABLE IV

Performance of BHS-FEST Filter For Three Stage Countercurrent Washing

| Example No. | Wash Ratio lb wash to OX per lb TA* | Dry Rate SCFH | HAc on Cake, ppmw wet | Cake Wetness wt % | HAC on Cake, ppmw dry |
|---|---|---|---|---|---|
| 27 | 0.2926 | 50 | 2800 | 12.9 | 3214 |
| 28 | 0.3406 | 50 | 2300 | 12.1 | 2616 |
| 29 | 0.2625 | 50 | 2500 | 12.0 | 2840 |
| 30 | 0.2633 | 50 | 3300 | 12.3 | 3762 |
| 31 | 0.2667 | 50 | 2300 | 12.1 | 2616 |
| 32 | 0.3266 | 35 | 3800 | 11.9 | 4313 |
| 33 | 0.2786 | 20 | 3500 | 12.0 | 3977 |
| 34 | 0.1573 | 20 | 4000 | 15.4 | 5361 |
| 35 | 0.3211 | 20 | 1700 | 13.6 | 1967 |
| 36 | 0.2607 | 20 | 3200 | 11.7 | 4086 |
| 37 | 0.3260 | 30 | 2000 | 12.6 | 2288 |
| 38 | 0.2581 | 30 | 4500 | 12.1 | 5119 |
| 39 | 0.2549 | 30 | 3000 | 12.0 | 3409 |

*lb. water recycled to the p-xylene oxidation process which must be removed (by distillation) per lb. TA processed by the filter.

We claim:

1. A process for the preparation of a crude aromatic polycarboxylic acid obtained by oxidizing an alkyl aromatic hydrocarbon to a polycarboxylic acid in the presence of an aliphatic carboxylic acid of 1 to 5 carbon atoms to prepare the crude polycarboxylic acid wherein the concentration of the aliphatic carboxylic acid in mother liquor retained by the crude polycarboxylic acid is equal to or less than about 5000 ppmw, based upon the weight of the crude polycarboxylic acid present, the aliphatic carboxylic acid being replaced by water, which process comprises:

(a) introducing a stream of a slurry of a crude aromatic polycarboxylic acid in a mother liquor comprising an aliphatic carboxylic acid having from 1 to 5 carbon atoms into a filter cell or a series of filter cells maintained in a suitable position whereby each filter cell develops a filter cake in the filter cells upon introduction of the slurry into each filter cell;

(b) interrupting the stream of the slurry into each filter cell upon development of the filter cake;

(c) introducing a water stream into each filter cell so as to form a reservoir of water in the filter cells sufficient in depth over the filter cake to cover the filter cake and water pressure is in a range above system pressure sufficient to displace the aliphatic carboxylic acid by positive pressure displacement from the filter cake;

(d) displacing the aliphatic carboxylic acid by positive pressure displacement from the filter cake;

(e) repeating steps (c) and (d) to successively wash filter cake into filter cells having successively increasing content of the aliphatic acid in a countercurrent method to wash filter cake in each filter cell in reverse order to degree of contamination by the aliphatic carboxylic acid; and (f) discharging the crude aromatic polycarboxylic acid containing 5000 ppmw, or less, in retained mother liquor of the aliphatic acid from the series of the filter cells.

2. The process of claim 1 wherein the alkyl aromatic hydrocarbon is selected from the group consisting of paraxylene, metaxylene, diisopropylbenzene, diethylbenzene, and 2,6-dimethylnaphthalene.

3. The process of claim 1 wherein the introduction of the water stream of step (c) and the displacing of the aliphatic carboxylic acid of step (d) is repeated to decrease the concentration of the aliphatic carboxylic acid in the filter cake to about 5000 ppmw, or less, based on the weight of crude polycarboxylic acid present, wherein said filter cake is washed in the countercurrent method.

4. The process of claim 1 wherein the alkyl aromatic hydrocarbon is paraxylene, the aliphatic carboxylic acid is acetic acid, and the crude aromatic polycarboxylic acid is crude terephthalic acid.

5. The process of claim 3 wherein the alkyl aromatic hydrocarbon is paraxylene, said aliphatic carboxylic acid of 1 to 5 carbon atoms is acetic acid and said crude aromatic polycarboxylic acid is crude terephthalic acid.

6. The process of claim 1 wherein depth of the filter cake is from about 0.5 inch to about 8 inches.

7. The process of claim 6 wherein depth of the filter cake is from about 2 to about 8 inches.

8. The process of claim 1 wherein the water pressure is in the range of from about 0.5 to about 65 psi above system pressure.

* * * * *